US00PP18252P3

(12) United States Plant Patent
Vorsa

(10) Patent No.: US PP18,252 P3
(45) Date of Patent: Nov. 27, 2007

(54) CRANBERRY VARIETY NAMED 'NJS98-23'

(50) Latin Name: ***Vaccinium macrocarpon* Ait.**
Varietal Denomination: NJS98-23

(75) Inventor: Nicholi Vorsa, Atco, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 7 days.

(21) Appl. No.: 11/355,602

(22) Filed: Feb. 15, 2006

(65) Prior Publication Data

US 2007/0192913 P1 Aug. 16, 2007

(51) Int. Cl.
*A01H 5/00* (2006.01)

(52) U.S. Cl. ..... Plt./156

(58) Field of Classification Search ..... Plt./156
See application file for complete search history.

*Primary Examiner*—Kent Bell
*Assistant Examiner*—S. B. McCormick-Ewoldt
(74) *Attorney, Agent, or Firm*—Klarquist Sparkman, LLP

(57) ABSTRACT

A new cranberry variety distinguished by significantly higher yields, higher anthocyanin (red pigment) content, and higher stolon vigor as compared to the currently cultivated commercial varieties.

4 Drawing Sheets

STATEMENT REGARDING FEDERALLY SPONSORED RESEARCH OR DEVELOPMENT

This invention was made in part with United States Government support awarded by the U.S. Department of Agriculture, Cooperative State Research, Education and Extension Service, under grant SRG 88-34155-3491.

Latin name of the genus and species of the plant claimed: *Vaccinium macrocarpon* Ait.

Variety denomination: 'NJS98-23'.

BACKGROUND

The present invention relates to a new and distinctive American cranberry variety having a combination of traits including significantly higher yields, higher anthocyanin (red pigment) content, and higher stolon vigor as compared to the currently cultivated commercial varieties. The new variety, 'NJS98-23', resulted from crossing the variety 'Stevens' (unpatented) as the seed parent, with the variety 'Ben Lear' (unpatented) as the pollen parent. The plant was originally selected from over 1,500 seedlings growing in test plots in Chatsworth, N.J. and Portage County, Wis.

The American cranberry (*Vaccinium macrocarpon* Ait.) is a temperate, woody perennial plant species native to North America. The United States is the largest producer, with Wisconsin and Massachusetts representing the majority of cranberry acreage and production, followed by New Jersey, Oregon and Washington. Currently grown cranberry varieties include selections from native populations, and first generation hybrids. Significant acreage is still devoted to varieties that were selected from native cranberry populations from as far back as 1850, including 'Ben Lear' (unpatented), 'Early Black' (unpatented), 'Howes' (unpatented), 'Lemunyon' (unpatented), 'McFarlin' (unpatented), and 'Searles' (unpatented). The hybrid varieties were developed from one cycle of breeding and selection that was conducted by the United States Department of Agriculture, in cooperation with state Agricultural Experiment Stations in the 1940's. This breeding program released a series of unpatented varieties in the 1950's including the most widely grown cultivar 'Stevens' (unpatented), which was selected from test plots in Pemberton, N.J.

Varieties having high anthocyanin production along with consistently high productivity have become essential for commercial success in cranberry production. Fruit crop productivity is a function of inherent differences among varieties for traits such as stolon vigor, upright density, inflorescence bud production, fruit set, and fruit size. Varieties with high stolon vigor will establish more rapidly and reduce the number of years required to achieve maximal production. However, after bed establishment, varieties must transition to optimal sexual reproduction mode, and optimal upright density, to achieve high crop production. Cranberry inflorescence bud primordia are set on uprights during the completion of the fruit development period and overwinter in a dormant state, before resuming growth the subsequent spring. Thus, the crop load of a given year, may impact the subsequent year's crop, contributing to the pronounced biennial bearing habit common to many varieties. Productivity is also subject to environmental effects, such as heat and light intensity stresses, cold (frost) stress, water stress (drought and excess), disease, insects, and certain pesticides.

TAcy, fruit anthocyanin content, is currently a fruit quality component of processed cranberries, having a minimum acceptable value, as well as premiums for fruit with higher TAcy values. Upon delivery to the processing plant, cranberries from a given bed are measured for TAcy content. TAcy is measured in terms of mg of anthocyanin per 100 g fruit using a standard spectrophotometric (520 nm) method. Earlier ripening varieties, which typically have higher TAcy, allow for earlier harvesting of a crop. Anthocyanin synthesis occurs predominately in the fruit epidermis, resulting in a generally negative correlation between fruit size and TAcy. The Rutgers University cranberry breeding program quantitatively measured TAcy along with mean fruit size, and selected only those progeny that were above the regression line representing the mean relationship between fruit size and TAcy.

New Jersey uniquely offers an ideal environment for cranberry breeding because of the climate, soils and water. Of all the cranberry production areas in North America, New Jersey conditions subject the cranberry to the highest disease pressure and heat stress. The plant must tolerate high heat stress and vegetative diseases during the growing season. Over 15 pathogens are known to incite cranberry fruit rot in New Jersey, and the fruit is also subject to heat scald and physiological breakdown. Thus, selection under New Jersey conditions offers the best opportunity to identify varieties with higher resistance to disease, scald, and heat stress.

The Rutgers University cranberry breeding program, in Chatsworth, N.J., was initiated in 1985 to take advantage of this unique selection pressure. The program's methods were designed to duplicate, as much as possible, the environment of a commercial bed. Thus, breeding plots of 1.5×1.5 m were established with multiple plants and allowed to fill in to form a dense canopy. Two to four years after planting, yield of a given plot was evaluated over a four year minimum to provide for biennial bearing assessment. Traits being evaluated in Rutgers University's cranberry breeding program include yield, fruit rot susceptibility/resistance, scald, stolon and upright vigor, total anthocyanin content (TAcy), soluble solids (Brix), and titratable acidity.

The new variety, 'NJS98-23', resulted from crossing the variety 'Stevens' (unpatented) as the seed parent, with the variety 'Ben Lear' (unpatented) as the pollen parent. The original plant of the new variety was selected from plants growing in cultured test plots planted in 1993 in Chatsworth, N.J.

'NJS98-23' is a new cranberry variety selected under New Jersey's stressful conditions, which offers the potential for rapid bed establishment, high yields, early ripening and higher TAcy content.

BRIEF SUMMARY

The 'NJS98-23' variety is distinguished from other cranberry varieties due to the following unique combination of characteristics: significantly higher yield, higher total anthocyanins, and greater stolon vigor.

'NJS98-23' has been asexually reproduced by cuttings at the Marucci Center for Blueberry and Cranberry Research and Extension Center, Chatsworth, N.J. since 1992. Over that period, no evidence of off-types of 'NJS98-23' has been observed or reported to us. Thus, it is concluded that 'NJS98-23' is stable and reproduces true to type in successive generations of asexual reproduction.

The following detailed description concerns the variety 'NJS98-23'. The original plant and vegetative propagules have been observed growing in cultivated areas in Chatsworth and Browns Mills, N.J., and Portage County and City Point, Wis. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless then context clearly indicates otherwise. Color designations are made with reference to The Royal Horticultural Society (R.H.S.) Colour Chart.

The colors of illustrations of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJS98-23' variety is based on observations of plants growing in the field in Chatsworth, N.J. and City Point, Wis. The characteristics of the variety were compared to its parents, 'Stevens' (unpatented) and 'Ben Lear' (unpatented), two of the most widely used cranberry varieties. The observed propagules were 3–8 years of age.

Scientific name: *Vaccinium macrocarpon* Ait.

Parentage:

*Seed parent.*—The variety 'Stevens' (unpatented) (derived from a McFarlin×Potter cross, both unpatented).

*Pollen parent.*—The variety 'Ben Lear' (unpatented) (selected from the wild in 1900 in Berlin, Wis.).

Figure 1:
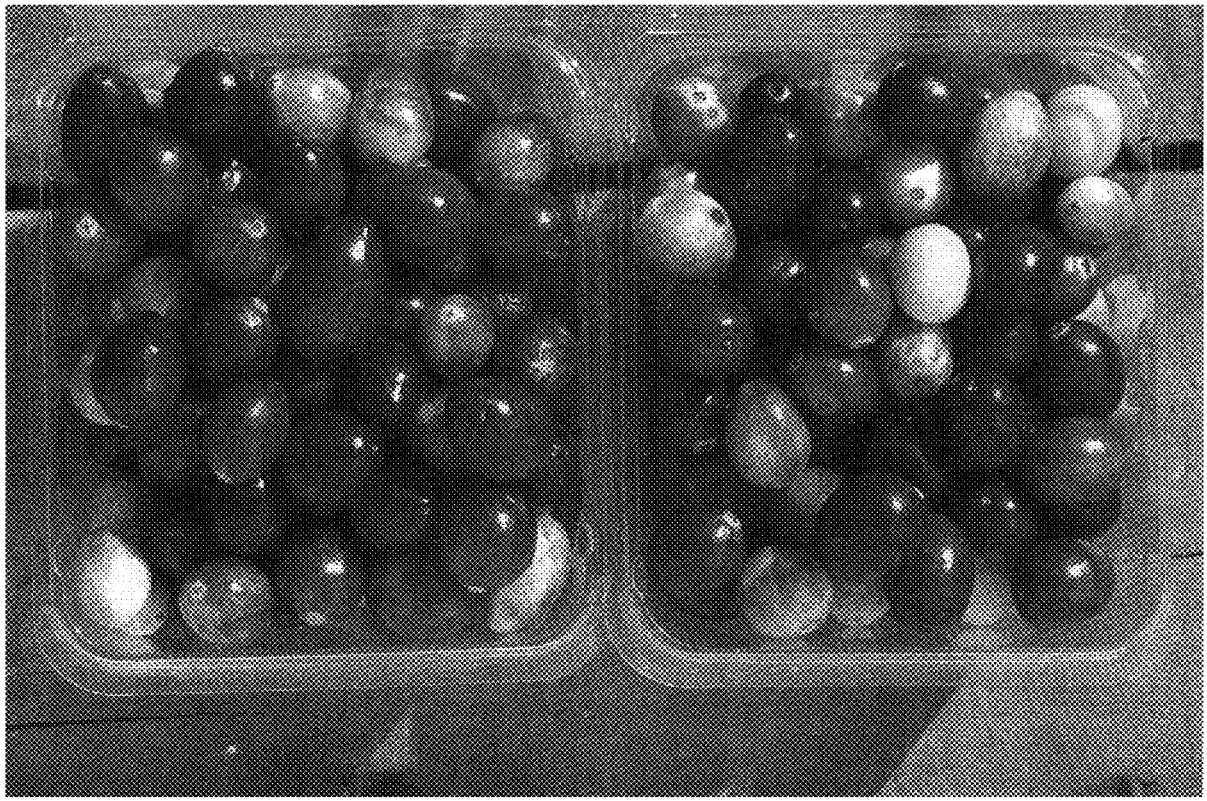
FIG. 1 is a color photograph of containers containing typical cranberries from the new variety 'NJS98-23' (left) compared to typical cranberries from the 'Stevens' variety (right). All cranberries were harvested Oct. 4, 2004 from the same cranberry bed in Chatsworth, N.J.
Figure 2:
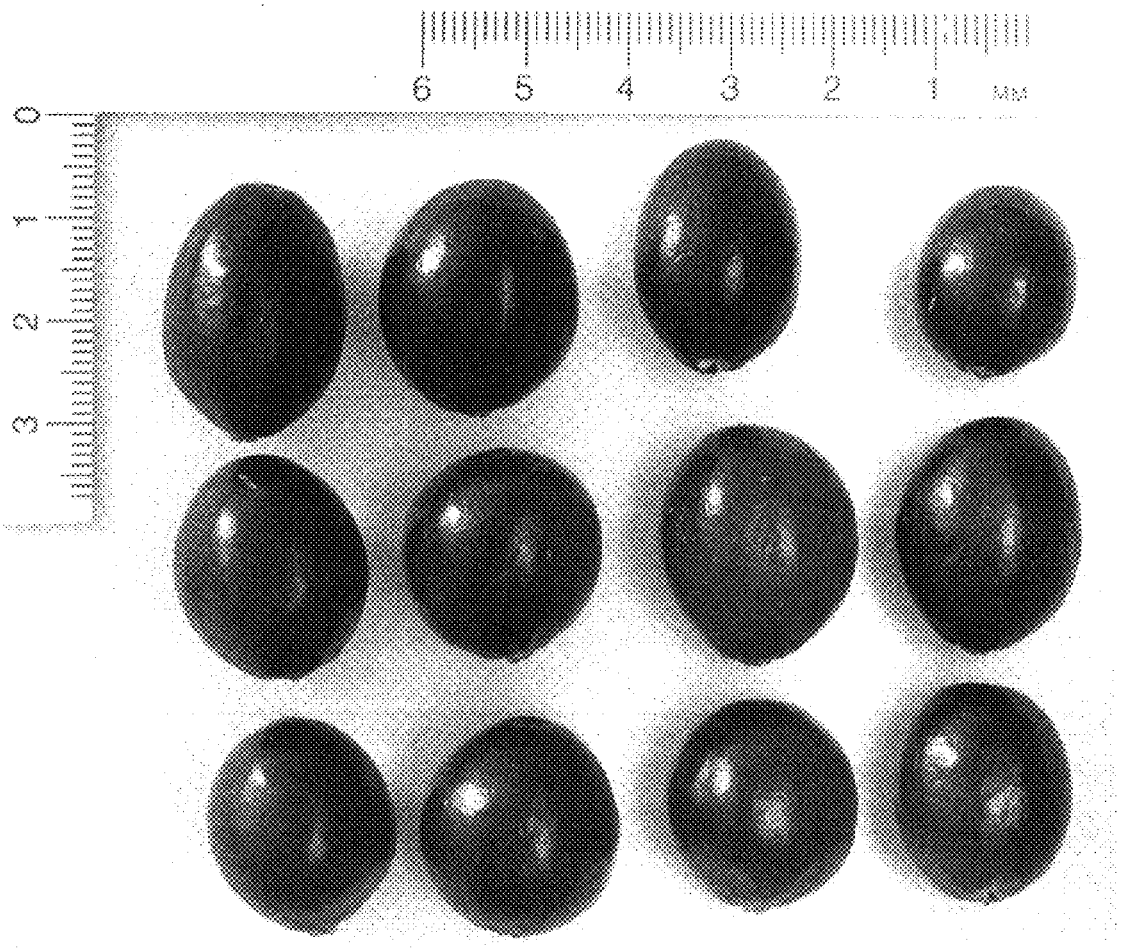
FIG. 2 is a color photograph showing a close up view of a number of representative cranberries from the new variety 'NJS98-23', demonstrating the size, shape and color of fruit. Cranberries harvested October 2005 from City Point, Wis.
Figure 3:
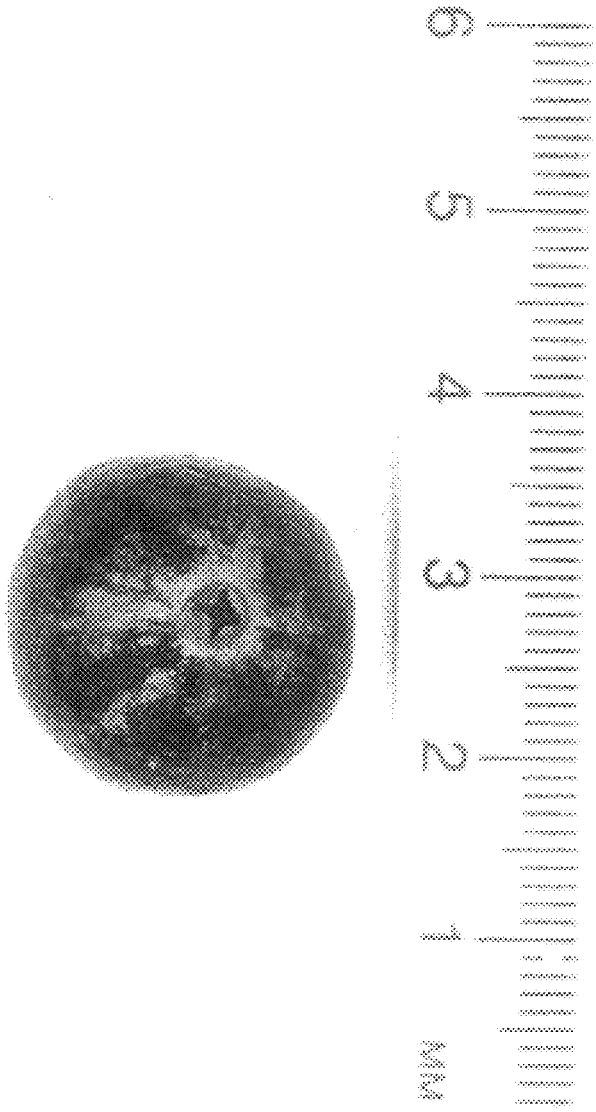
FIG. 3 is a color photograph showing a close up view of a bloom on the calyx end of 'NJS98-23' berries.
Figures 4A, 4B:
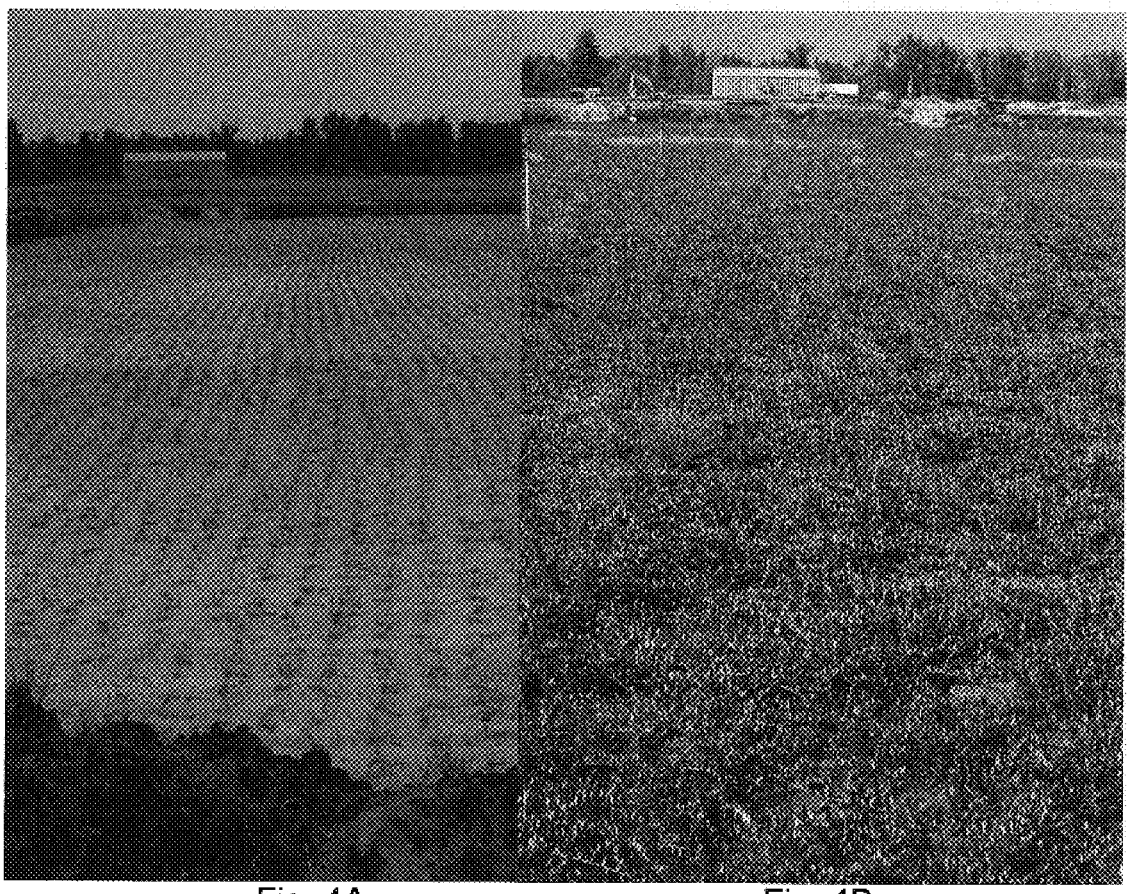
FIG. 4 is a color photograph showing a bed of 'NJS98-23' planted with rooted cuttings in mid June 2005 in City Point, Wis. (A) was taken Jun. 28, 2005, and (B) was taken 3 months later, Oct. 4, 2005, and shows the extensive vine growth and coverage of the bed.

Plant:

*Vigor.*—In a replicated trial planted Jun. 16, 2003 and consisting of 80 advanced selections and standard varieties, 'NJS98-23' had the highest percent cover, 45%, on Jun. 21, 2004, compared to 'Stevens' with 23% cover and 'Ben Lear' with 28% cover. General observations of 'NJS98-23' plantings indicate exceptional plant vigor (FIG. 4).

*Growth habit.*—Trailing shrub with very slender stems.

*Reproductive structures.*—The cranberry plant has both asexual (stolons) and sexual reproductive (fruit) structures. Asexual propagation can be generated from three types of vegetative buds, terminal, axillary and adventitious. Therefore, the entire above-ground portion of the cranberry plant can be considered a reproductive structure. Cranberry stolons readily root when in contact with soil. Cranberries also reproduce from seeds. Cranberry cultivars are propagated asexually through rooting of stolons and vertical shoots. Cranberry growers typically reproduce cranberries with either rooted or unrooted cuttings, or vine prunings that are broadcast and then pressed into the soil surface.

*Runner length.*—Average runner (stolon) length was 26.2 cm in a 2-year old field planting.

*Upright height.*—Average upright height was 10.2 cm at 1.5 years old.

*Stem diameter.*—1.5 mm at base of current year's growth.

*Internodes.*—Average internode length was about 7.5 mm on a 1-year old runner.

*Productivity.*—In established test plots in Chatsworth, N.J., 'NJS98-23' produced an average of 325 g of berries/sq. ft. (35 g/dm$^2$) in comparison to 'Stevens' yield of 280 g/sq. ft. (30 g/dm$^2$) (4-year averages, see Table 1). In established plots in City Point, Wis., 'NJS98-23' produced an average of 325 g of berries/sq. ft. (35 g/dm$^2$) in comparison to 'Stevens', 226 g/sq. ft. (24 g/dm$^2$), and 'Ben Lear', 289 g/sq. ft. (31 g/dm$^2$) (4-year averages, see Table 2).

*Hardiness.*—Zones 4–7 (from USDA Misc. Publ. 814).

*Disease resistance.*—Susceptibility of 'NJS98-23' to vegetative and root diseases was comparable to that of 'Stevens' (unpatented) and 'Ben Lear' (unpatented).

Leaves: The length, width and other measurements were obtained from observations of 20 typical fully developed leaves on Nov. 16, 2004 from a 6-yr. old field plot. Color was determined on actively growing plants.

*Texture.*—Coriaceous (leathery).

*Length.*—About 10.3 mm to about 12.8 mm, averaging about 11.5 mm.

*Width.*—About 3.5 mm to about 5.2 mm, averaging about 4.4 mm.

*Shape.*—Elliptic (2.6:1 ratio).

*Apex shape.*—Rounded.

*Base shape.*—Rounded, nearly sessile.

*Margin.*—Entire, slightly revolute.

*Leaf color.*—Upper leaf surface color ranges from bright green (RHS 143C, green group) in new growth to deep green in mature leaves (RHS 139A, green group).

*Pubescence.*—A small number of non-glandular trichomes found at tip and margins of leaf.

Flowers:

*Size and shape.*—Slender, nodding flowers on erect pedicels and in clusters of 3–5 flowers, corolla long-conic in bud, petals divided nearly to the base when open; typical open flower measuring about 10 mm across.

*Color.*—Unopened bud: deep pink (RHS 68C, red-purple group). Opened flower: pale pink (RHS 69A & B, red-purple group).

*Petals.*—4 petals per flower; narrow and revolute in shape.

*Bloom season.*—Bloom typically begins in late May and continuous until early July depending on the season. 'NJS98-23' reached 50% bloom on Jun. 24, 2003, Jun. 7, 2004, and about Jun. 20, 2005; 2–3 days before Stevens each year.

*Mean number of flowers per upright.*—4.2.

Fruit: Observations are from 30 typical fruit harvested from test plots in Chatsworth, N.J. and 30 fruit from City Point, Wis. on Oct. 10, 2004.

*Shape.*—Elliptic, with rounded to slightly pointed stem end, and rounded calyx end.

*Size.*—In N.J., 2.1 cm long and 1.7 cm wide; in Wis., 2.0 cm long and 1.6 cm wide.

*Skin.*—Shiny, bloom around calyx end, otherwise with little to no bloom.

*Fruit skin color.*—Ranged from RHS 46A (red group) for the lightest berries, RHS 53A (red group) for medium berries, to RHS 187A (greyed-purple group) for the darkest (harvested Oct. 10, 2004, stored at 4° C., evaluated Dec. 22, 2004).

*Fruit flesh color.*—Ranged from RHS N155C to RHS N155D (white group).

*Stem pit.*—Medium in size (diameter 1.12 mm, similar to Stevens, 1.08 mm). Stem pit end slightly indented.

*Average weight.*—In N.J., 2.2 g; in Wis., 2.0 g. Fruit collected yearly from 1 ft$^2$ samples in test plots had an average weight of 2.3 g in N.J. and 1.9 in Wis. (Tables 1 & 2).

*Number of seeds.*—An average of 20 seeds per fruit, similar to 'Stevens' (unpatented) and more than 'Ben Lear' (unpatented).

*Seed color.*—Ranged from RHS 165B to RHS 174B (greyed-orange group).

*Seed size.*—Mean diameter, 1.27 mm (n=10); mean length, 2.18 mm (n=10); mean weight, 1.46 mg (n=20).

*Fruit chemistry.*—100 g samples of fruit were harvested each year from test plots in Chatsworth, N.J. and City Point, Wis. and evaluated for fruit chemistry. In Wisconsin, fruit harvested from 'NJS98-23' consistently had double the TAcy values as 'Stevens'; and in New Jersey, 'NJS98-23' had TAcy values 50% greater than 'Stevens' (Tables 3 & 4). 'NJS98-23' had Brix, titratable acidity, and proanthocyanidin values that were comparable to 'Stevens' in Wisconsin and New Jersey trials.

*Fruit production.*—First picking date in New Jersey was September 10, and last picking date was October 25. Average production was 325 g of berries/ft2 (35 g/dm2), equivalent to 313 barrels/acre (4 yr. mean in both N.J. and Wis. test plots, Table 1 & 2).

*Usage.*—Processing and fresh fruit.

*Disease resistance.*—In the Wisconsin trial, 'NJS98-23' had 11% fruit rot (mean of October 2001, 2002, and 2005), comparable to 'Ben Lear' (unpatented), and slightly more than 'Stevens' (unpatented). In New Jersey, where disease pressure is greater, 'NJS98-23' had an average of 20% fruit rot (2001–2004) relative to 'Stevens' (unpatented) at 9%.

TABLE 1

Yield and fruit weight comparisons from a research trial established May 1999 in Chatsworth, NJ.

| Cultivar | 2001 Mean | 2002 25-Oct | 2003 mean | 2004 mean | 01-04 Mean |
|---|---|---|---|---|---|
| | | Total yield, g/ft$^2$ | | | |
| 'NJS98-23' | 375 | 224 | 370 | 332 | 325 |
| 'Stevens' | 210 | 227 | 336 | 348 | 280 |
| | | Fruit wt., g/berry | | | |
| 'NJS98-23' | 2.2 | 2.5 | 2.4 | 2.1 | 2.3 |
| 'Stevens' | 2.2 | 2.2 | 2.3 | 1.8 | 2.1 |

TABLE 2

Yield and fruit weight comparisons from a replicated trial established May 1999 in City Point, WI.

| Cultivar | 4-Oct 2002 | 9-Oct 2003 | 9-Oct 2004 | Mean 2005* | 02-05 Mean |
|---|---|---|---|---|---|
| | | Total yield, g/ft$^2$ | | | |
| 'NJS98-23' | 216 | 317 | 442 | 325 | 325 |
| 'Ben Lear' | 189 | 273 | 338 | 356 | 289 |
| 'Stevens' | 106 | 197 | 374 | 229 | 226 |

TABLE 2-continued

Yield and fruit weight comparisons from a replicated trial established May 1999 in City Point, WI.

| Cultivar | 4-Oct 2002 | 9-Oct 2003 | 9-Oct 2004 | Mean 2005* | 02-05 Mean |
|---|---|---|---|---|---|
| | Fruit wt., g/berry | | | | |
| 'NJS98-23' | 1.9 | 1.9 | 1.9 | 1.8 | 1.9 |
| 'Ben Lear' | 2.0 | 1.6 | 1.5 | 1.6 | 1.7 |
| 'Stevens' | 1.8 | 1.8 | 1.7 | 1.7 | 1.8 |

*2005 mean of 3 dates, 19-Sep, 3-Oct, 15-Oct.

TABLE 3

Fruit color comparisons of 'NJS98-23' and 'Stevens' in 2001-2004, in Chatsworth, NJ.

| | Tacy, mg/100 g fruit | | | | | | | |
|---|---|---|---|---|---|---|---|---|
| Cultivar | 10-Sep 2001 | 15-Oct 2001 | 25-Oct 2002 | 15-Sep 2003 | 6-Oct 2003 | 24-Sep 2004 | 11-Oct 2004 | Oct mean 2001-04 |
| 'NJS98-23' | 32 | 52 | 66 | 23 | 45 | 40 | 47 | 52 |
| 'Stevens' | 5 | 37 | 44 | 4 | 27 | 11 | 24 | 34 |

TABLE 4

Comparison of fruit color of 'NJS98-23' with 'Ben Lear' and 'Stevens' in 2001-2005, in City Point, WI.

| | TAcy, mg/100 g fruit | | | | | |
|---|---|---|---|---|---|---|
| Cultivar | 19-Oct 2001 | 4-Oct 2002 | 9-Oct 2003 | 9-Oct 2004 | 3-Oct 2005 | 01-05 Mean |
| 'NJS98-23' | 51 | 52 | 44 | 67 | 36 | 50 |
| 'BenLear' | 60 | 40 | 46 | 56 | 32 | 47 |
| 'Stevens' | 26 | 26 | 27 | 35 | 12 | 25 |

I claim:

1. A new and distinct variety of cranberry plant, substantially as herein shown and described.

* * * * *